United States Patent [19]

Jacob et al.

[11] Patent Number: 5,897,831
[45] Date of Patent: *Apr. 27, 1999

[54] PROCESS FOR DRY STERILIZATION OF MEDICAL DEVICES AND MATERIALS

[75] Inventors: Adir Jacob, 23 Juniper La., Framingham, Mass. 01701; Jonathan Allen Wilder, Rochester, N.Y.

[73] Assignee: Adir Jacob, Framingham, Mass.

[ * ] Notice: This patent is subject to a terminal disclaimer.

[21] Appl. No.: 08/478,253

[22] Filed: Jun. 7, 1995

Related U.S. Application Data

[60] Continuation-in-part of application No. 08/221,843, Apr. 1, 1994, Pat. No. 5,451,368, which is a division of application No. 08/042,136, Apr. 2, 1993, Pat. No. 5,302,343, which is a continuation of application No. 07/762,573, Sep. 19, 1991, Pat. No. 5,200,158, which is a continuation of application No. 07/562,392, Aug. 3, 1990, Pat. No. 5,171,525, which is a continuation of application No. 07/331,438, Mar. 31, 1989, Pat. No. 4,979,920, which is a continuation-in-part of application No. 07/072,899, Jul. 14, 1987, Pat. No. 4,818,488, which is a continuation-in-part of application No. 07/019,134, Feb. 25, 1987, Pat. No. 4,801,427.

[51] Int. Cl.⁶ .................. A61L 2/00; A61L 2/14

[52] U.S. Cl. .................. 422/22; 422/23; 422/28; 250/455.11; 204/164

[58] Field of Search .................. 422/22, 23, 28; 250/455.11; 204/164

[56] References Cited

U.S. PATENT DOCUMENTS

| | | | |
|---|---|---|---|
| 4,801,427 | 1/1989 | Jacob | 422/23 |
| 4,909,995 | 3/1990 | Jacob | 422/186.29 |
| 5,084,239 | 1/1992 | Moulton et al. | 422/22 |
| 5,393,490 | 2/1995 | Jacob | 422/22 |
| 5,413,758 | 5/1995 | Caputo et al. | 422/22 |
| 5,453,125 | 9/1995 | Krough | 118/723 MR |

*Primary Examiner*—Lyle A. Alexander
*Attorney, Agent, or Firm*—Lahive & Cockfield, LLP

[57] ABSTRACT

Articles which it is intended to sterilize are placed into a confined volume and are subjected to neutral species of an electrical discharge while maintaining the volume glowless and substantially field free by interposing a barrier between the articles and the discharge, the barrier being transparent to neutral species and opaque to charged species emanating from the discharge.

20 Claims, 5 Drawing Sheets

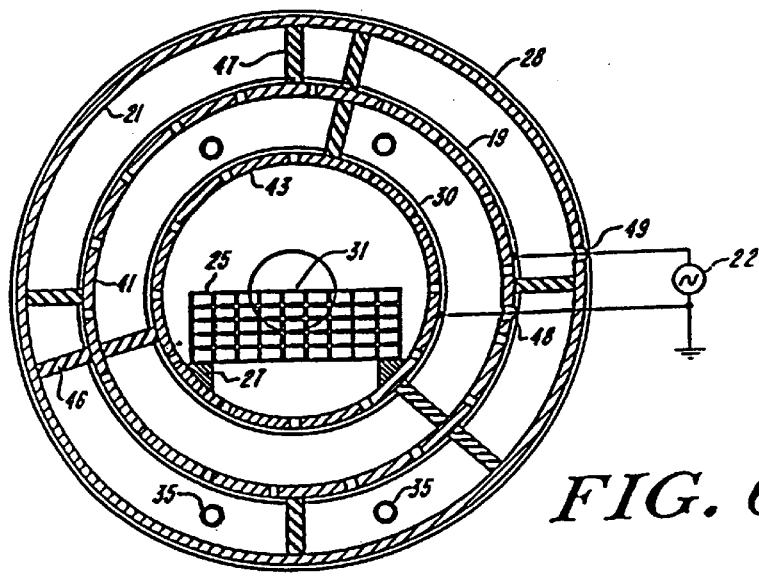
FIG. 6
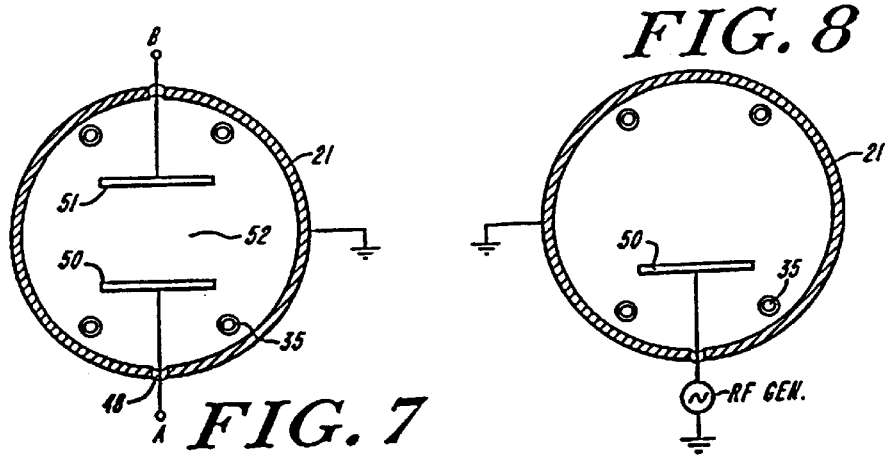
FIG. 8
FIG. 7
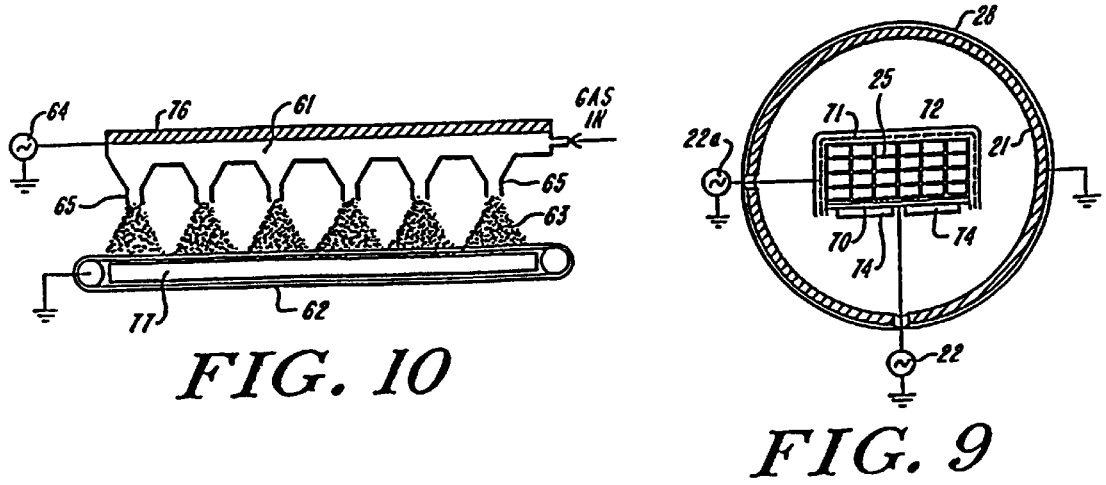
FIG. 10
FIG. 9

PROCESS FOR DRY STERILIZATION OF MEDICAL DEVICES AND MATERIALS

RELATED APPLICATIONS

This application is a continuation-in-part of Ser. No. 08/221,843, filed Apr. 1, 1994, now U.S. Pat. No. 5,451,368, which is a division of Ser. No. 08/042,136, filed Apr. 2, 1993, (now U.S. Pat. No. 5,302,343), which is a Continuation of Ser. No. 07/762,573, filed Sep. 19, 1991, (now U.S. Pat. No. 5,200,158), which is a Continuation of Ser. No. 07/562,392, filed Aug. 3, 1990 (now U.S. Pat. No. 5,171,525), which is a Continuation of Ser. No. 07/331,438, filed Mar. 31, 1989 (now U.S. Pat. No. 4,979,920), which is a Continuation-In-Part of Ser. No. 07/072,899, filed Jul. 14, 1987, (now U.S. Pat. No. 4,818,488), which is a Continuation-In-Part of Ser. No. 07/019,134, filed Feb. 25, 1987 (now U.S. Pat. No. 4,801,427).

BACKGROUND OF THE INVENTION

1. Field

This invention relates to plasma sterilization, and provides a method for exposing articles to be sterilized to substantially neutral species of a plasma in a field free, glowless volume.

2. State of the Art

Modern medical and dental practice require the use of aseptic materials and devices, many of them meant for repeat use. In order to achieve this sterilization, processes are needed, at the manufacturer, and also at the hospitals or dental offices for treatment of reusable materials and devices.

Typical of materials which are reused in the hospital environment and require repeated sterilization are major surgical instrument trays, minor surgical kits, respiratory sets, fiber optics (endoscopes, proctoscopes, angioscopes, bronchoscopies) and breast pumps. Typical instruments and devices which are reused in a dental environment and require repeated sterilization are hand-pieces, dental mirrors, plastic tips, model impressions and fabrics.

There are a wide variety of medical devices and materials that are to be supplied from the manufacturer already packaged and sterile. Many of these devices and materials are disposable. Typical of this group are barrier packs, head coverups and gowns, gloves, sutures, syringes and catheters.

One major sterilization process in present use is that which employs ethylene oxide (EtO) gas in combination with Freon-12 ($CCl_2F_2$) at up to three atmospheres of pressure in a special shatter-proof sterilization chamber. This process, in order to achieve effective asepsis levels, requires exposure of the materials to the gas for at least one to three hours followed by a minimum of twelve hours, or longer, aeration period. The initial gas exposure time is relatively long because the sterilization is effected by alkylation of amino groups in the proteinaceous structure of any microorganism. EtO sterilization requires the attachment of the entire EtO molecule, a polyatomic structure containing seven atoms to the protein. This is accompanied by the requirement of hydrogen atom rearrangement on the protein to enable the attachment of EtO. Because of kinetic space-hindrance factors governing the attachment of such a bulky molecule, the process needs to be carried out at high pressure and be extended over a long period of time. It is, therefore, deemed very inefficient by the industry at large.

Perhaps the chief drawback to this system, however, is its dangerous toxicity. Ethylene-oxide (EtO) is a highly toxic material dangerous to humans. It was recently declared a carcinogen as well as a mutagen. It requires a very thorough aeration process following the exposure of the medical materials to the gas in order to flush away toxic EtO residues and other toxic liquid by-products like ethylene glycol and ethylene chlorohydrin. Unfortunately, it is a characteristic of the gas and the process that EtO and its toxic by-products tend to remain on the surface of the materials being treated. Accordingly, longer and longer flush (aeration) times are required in order to lower the levels of these residues absorbed on the surface of the materials to a safe operational value. A typical volume for each batch using this EtO process is 0.2 to 50 cu. ft. within the health and dental care environments.

A number of other approaches for performing sterilization have also been employed. One such process is high pressure steam autoclaving. However, this requires high temperature and is not suitable for materials which are affected by either moisture or high temperature, e.g., corrodible and sharp-edged metals, plastic-made devices, etc., employed by the hospital and the dental communities.

Another approach utilizes either x-rays or radioactive sources. The x-ray approach is difficult and expensive. The use of radioactive sources requires expensive waste disposal procedures, as well as requiring radiation safety precautions. The radiation approach also presents problems because of radiation-induced molecular changes of some materials, which, for example, may render flexible materials brittle, e.g., catheters.

It is therefore a primary object of the present invention to provide a process and apparatus for dry sterilization of medical and dental devices and materials, which can be operated efficiently, both with respect to time and volume and which can be carried out below 70° C.

It is another object of the present invention to provide a safe, nontoxic, process for the sterilization and surface treatment of medical and dental devices and materials, a process which does not employ toxic feed gases and one which does not yield toxic absorbed surface residues and by-products.

SUMMARY OF THE INVENTION

Broadly speaking, in the present invention, sterilization or surface treatment is achieved by exposing the medical or dental devices and materials to a highly reducing gas plasma like that generated by gas discharging molecular hydrogen, or to a highly oxidizing gas plasma, for example, one containing oxygen. Depending on the specific sterilization requirements, a mildly oxidizing environment, somewhere between the environment offered by oxygen and that offered by hydrogen is presented by gas discharging molecular nitrogen, either in pure state, or in multicomponent mixtures with hydrogen or oxygen, supplemented by an inert gas. In such a manner, plasma discharge chemical-physical parameters can be adjusted to fit almost any practical application of sterilization and surface treatment.

Such a plasma is generated by creating an electrical discharge in a gaseous atmosphere maintained at sub-atmospheric or atmospheric pressure, within which the materials to be sterilized are placed.

Generation of gas plasmas is a very well developed discipline, which has been specifically employed in semiconductor processing. See, for example, U.S. Letters U.S. Pat. Nos. 3,951,709; 4,028,155; 4,353,777; 4,362,632; 4,505,782 and RE 30,505 assigned to one of the present inventors (Jacob).

In one instance the gas plasma sterilization process of this invention involves evacuating a chamber to a relatively low pressure after the devices or materials to be sterilized or treated have been placed within it.

An oxidizing gaseous atmosphere, as an example, is then provided to the chamber at a relatively low pressure, typically in the range 10 microns Hg to 10 torr, corresponding to a continuous gaseous flow rate range of 20 to 3000 standard cc per minute. An electrical discharge is produced within the chamber by conventional means, such as a microwave cavity or a radio frequency (RF) excited electrode. Alternatively, RF power in the power density range $0.0125–0.08$ W/cm$^3$ may be coupled into the gas via a single electrode disposed within the chamber in a nonsymmetrical electrical configuration, or via two electrodes contained within the chamber in an electrically symmetrical configuration. In either case the material to be sterilized is placed on one of the electrodes, while the chamber's wall is commonly maintained at ground potential.

The nonsymmetrical arrangement provides the basis for a low plasma potential mode of operation which is conducive to low sterilization temperatures and the suppression of otherwise deleterious ion bombardment and contamination of the devices and materials.

The resultant discharge produces a gas plasma including both excited electrically charged gaseous species and excited electrically neutral gaseous species. For example, free radicals of atomic oxygen as well as excited molecular oxygen are formed in a discharge through molecular oxygen. These oxygen-bearing active species interact chemically with the proteinaceous components of the microorganisms residing on the surfaces of medical or dental devices to be sterilized, thereby denaturing the proteinaceous molecules and achieving kill rates of microorganisms equivalent to a probability of microorganism survival of less than one in a million.

The efficiency of this process is due, in part, to the fact that the gaseous plasma entities are very reactive and atomically small (usually monoatomic or diatomic) and therefore exhibit an enhanced ability to chemically attach themselves to a proteinaceous structure and/or abstract (remove) hydrogen atoms from it. It was also ascertained that the presence of low levels of water vapor in the plasma feed gas enhances sterilization efficiency dramatically. It is believed that accentuation of active species concentration and/or favorable preconditioning of micro-organisms' proteinaceous structure occurs in the presence of moisture during the discharge process. These processes are responsible for the total kill of the microorganisms. The kinetic space (or steric) restriction for this type of interaction is at least one thousand times lower than that for EtO alkylation.

Several specific types of interaction take place. One specific interaction is hydrogen abstraction from amino groups. Another is rupturing ring structures, particularly those including nitrogen, or carbon-carbon bond cleavages. It is important to note that these processes produce only gaseous effluents, such as water vapor and carbon dioxide, which would not remain absorbed on the surface of medical devices, but would, instead, be carried away from such devices with the main gas stream to the pump.

This sterilization process may be used with pre-packaged materials, such as disposable or reusable devices contained within gas-permeable bags or pouches. With sealed pouches (e.g., polyethylene/Tyvek packaging), the barrier wall of the package is pervious to the relatively small active species of the sterilizing plasma, but impervious to the larger proteinaceous microorganisms. (Tyvek is a bonded polyolefin produced by DuPont.)

After evacuation of the chamber, and introduction of the gas or gas mixture, the gas(es) will permeate the package wall with a dynamic free exchange of gas(es) from within and from outside the package.

Upon striking a microwave or an RF discharge to form the plasma, and, depending upon electrical configuration and pressure, the plasma may actually be created within and outside the package or, alternatively, the package may be placed in a substantially electrically shielded (field-free) glowless zone, so that it is subject to predominantly electrically neutral, rather than electrically charged, active species which pass through the packaging wall to interact with the surface of the materials it contains.

In yet a different electrical configuration, the packages containing devices to be sterilized can be placed on a conveyor belt and swept into an atmospheric pressure corona discharge gap operated in ambient air. With this configuration, the discharge electrodes are comprised of a grounded metal-backed conveyor belt forming the bottom electrode, while the top electrode is comprised of a metal block with multiple needle-like nozzles for the dispersion of gas into the discharge gap.

Sterilization with this continuous, in-line, apparatus, is brought about by either ozone formation, due to presence of discharged oxygen in air, or due to any other oxidizing gas mixture that can be introduced into the discharge gap via a plurality of nozzles, which are an integral part of the top electrode.

This corona discharge will normally operate in the power density range 5–15 W/cm$^2$ and in the frequency range 10–100 KHz and 13–27 MHz, associated with gas flows in the range of several standard liters per second.

For example, in order to enable device sterilization by a strongly oxidizing plasma when employing the process with a polyethylene-based packaging, it is necessary to provide that oxygen-bearing active species can permeate through the organic package barrier in the first place, and that a sufficient number of these species traverse that barrier in order to effectively kill all microorganisms on a medical or dental device enclosed within the pouch.

Relevant strongly reducing, oxidizing, mildly oxidizing or mildly reducing conditions can be obtained by plasma discharging diatomic gases like hydrogen, oxygen, nitrogen, halogens, or binary mixtures of oxygen and hydrogen, oxygen and nitrogen (e.g., air), oxygen and inert gases, or the gaseous combination of oxygen, nitrogen and inert gases like helium or argon, depending on the particular substances to be sterilized or treated.

The predominance of oxygen in the above mixtures is preferred but not mandatory. A predominance of nitrogen, for example, will result in mildly oxidizing conditions, but in somewhat higher process temperatures during sterilization for a given reaction pressure and power density. The inert gas fraction can be variable in the range 10 to 95%; the higher the fraction, the lower the processing temperature for a given pressure and power density. However, sterilization exposure time increases the higher the inert gas fraction in the mix. Substitution of argon for helium, for example, will result in higher sterilization temperatures for a given pressure and power density. In this case, instability of the gas discharge operation may set in, requiring a power density increase at a given pressure, compared to that employed with helium, resulting in higher process temperatures.

Effective sterilization can also be obtained with a pure reducing hydrogen plasma or with a plasma discharge through pure inert gases like for example, helium, argon, and their mixtures, due to their very strong hydrogen atom abstraction (removal) capabilities from proteinaceous structures of microorganisms. The addition of pure helium to an argon sterilizing plasma will enhance the stability of the latter and reduce overall sterilization temperatures. Hydrogen and its mixtures with either nitrogen or oxygen, or with both, in the presence or absence of an inert gas, will show effective sterilization capabilities over a wide range of concentrations in these mixtures, thereby enhancing sterilization process flexibility and versatility.

A first objective of facilitating the gaseous permeation through an organic barrier (e.g., plastic or paper) is accomplished by evacuating the chamber (containing the loaded pouches) to a base pressure of approximately 20 microns Hg. This rids the pouches of previously entrapped atmospheric air, and equalizes the pressure inside the pouch to that inside the chamber (across the organic barrier). The subsequent introduction into the chamber of an oxygen-containing gas, in a typical situation, will establish an instantaneous higher pressure inside the chamber (outside the pouch) relative to that inside the pouch. This pressure gradient across the pouches' barrier will serve as the initial driving force of gas into the pouch. At an equilibrated state, an active and ongoing interchange of molecules across the barrier will take place, attempting at all times to maintain the same pressure on both sides of the organic barrier. Upon striking a discharge through this gas, oxygen-bearing active species will be generated. Typically, these active species will be deactivated in large amounts by the organic barrier or due to interaction with neighboring metallic surfaces. This will commonly substantially reduce the availability of these active species to do the sterilizing job.

In order to accomplish the objective of generating a sufficient number of reactive species traversing the organic barrier of a package to effect efficient sterilization cycles, the plasma discharging of gaseous moisture mixtures proved extremely beneficial. Plasma discharging of various innocuous gases containing moisture levels in the range 100 to 10,000 ppm of water vapor enabled the accentuation of active species concentration by more than a factor of two, thereby substantially shortening sterilization exposure times. Consequently, in a few system configurations which were previously characterized by relatively high processing temperatures, process temperatures were now kept sufficiently low due to the shortened sterilization cycles. Effective binary moisture mixtures were those comprised of oxygen, nitrogen, hydrogen and argon. Ternary moisture mixtures of nitrogen-oxygen and argon-oxygen were somewhat more effective at similar power densities than moisture mixtures of pure nitrogen or pure argon. Moisture mixtures containing halogens although very effective, were too corrosive and toxic. The most effective moisture mixture was that of oxygen, reducing sterilization cycles by more than a factor of two.

In addition, it was found that the organic barrier of a packaging pouch could be passivated in such a way as to substantially reduce its take-up of oxygen-bearing active species needed as a sterilizing agent and one which must render a final non-toxic medical device, without the formation of any toxic by-products.

One such passivation method consists of simultaneously introducing into the chamber a gaseous mixture, which in addition to oxygen-containing gas(es), also contains selected other gases as set forth below:

1. Organohalogens, based on carbon and/or silicon, attached to any of the known halogens. Particularly those organic compounds of carbon and/or silicon that are saturated or unsaturated and contain in their molecular structures one (1) or two (2) carbon or silicon atoms attached to: a predominance of fluorine atoms; a predominance of chlorine atoms; a predominance of bromine or iodine atoms; an equal number of fluorine and chlorine atoms simultaneously; an equal number of chlorine and bromine atoms simultaneously; an equal number of fluorine and bromine atoms simultaneously; an equal number of fluorine and iodine atoms simultaneously; an equal number of chlorine and iodine atoms simultaneously. A predominance of fluorine in these compounds includes structures where all other atoms attached to a carbon or a silicon atom can be all the other halogens, or only one or two other halogens out of the four halogens known, in conjunction with other atoms, as for example hydrogen. The same comments apply to a predominance of chlorine, bromine and iodine. For the latter, however, the simultaneous presence of bromine is unlikely to be practical due to a low volatility of the structure, but the simultaneous presence of fluorine or chlorine, or both, is practical. It is worth noting that hydrogen-containing organohalogens will have a tendency to polymerize under plasma conditions, and in some cases, be flammable in as-received condition.

Most effective sterilizing mixtures of oxygen and an organohalogen are those where the organohalogen is a mixture of organohalogens in itself, either based on carbon and/or silicon, where the oxygen fraction is over 70% by volume; yet sterilization will be effected for lower oxygen content at the expense of excessive halogenation of the surface of the material to be sterilized, and at the expense of excessive loss of transparency of the wrapping pouch.

2. Organohalogens in conjunction with either nitrogen or an inert gas like helium or argon. In these cases, it is considered practical to keep the fraction of the inert gas in predominance in order to keep the process temperature as low as possible. Inert gas fractions up to 95% by volume will be effective in killing microorganisms. The nitrogen fraction is ideally kept below that of the oxygen fraction.

3. Inorganic halogens, defined as compounds not containing carbon or silicon, but preferably containing as the central atom or atoms either hydrogen, nitrogen, sulfur, boron, or phosphorus linked to any of the known halogens in a similar manner as described for the organohalogens under item 1 above, or defined as compounds that contain only halogens without a different central atom, like for example molecular halogens (e.g., $F_2$, $Cl_2$) and the interhalogens which contain two dissimilar halogen atoms (e.g., Cl-F, I-F, Br-Cl based compounds, etc.). Also in this case the inorganic halogen maybe, in itself, a mixture of different inorganic halogens as defined above.

Most effective sterilizing mixtures of oxygen and an inorganic halogen are those where the oxygen fraction is over 80% by volume; yet sterilization will be effected for lower oxygen content at the expense of excessive halogenation of the surface of the material to be sterilized, and at the expense of excessive loss of transparency of the wrapping pouch.

4. Inorganic halogens in conjunction with either nitrogen or an inert gas as described in item 2 above.

5. Inorganic oxyhalogenated compounds, not containing carbon or silicon, but preferably contain either nitrogen, phosphorus, or sulfur, each of which is simultaneously attached to oxygen and a halogen (e.g., NOCl, $SOCl_2$, $POCl_3$, etc.). More specifically, the nitrogen-oxygen, or the sulfur-oxygen, or the phosphorus-oxygen entities in the previous examples are linked to any of the known halogens in a similar manner as described for the organohalogens under item 1 above. The inorganic oxyhalogenated fraction may be, in itself, a mixture of different inorganic oxyhalogenated compounds as deemed above.

Most effective sterilizing mixtures of oxygen and an inorganic oxyhalogenated structure are those where the oxygen fraction is over 70% by volume; yet effective sterilization will be obtained for lower oxygen content at the expense of excessive halogenation of the surface to be sterilized, and at the expense of excessive loss of transparency of the wrapping pouch.

6. Inorganic oxyhalogenated compounds in conjunction with free nitrogen or an inert gas as described in item 2 above.

7. Multicomponent mixtures comprised of members in each of the aforementioned groups. The simultaneous presence of free nitrogen and an inert gas like helium or argon in any of the above mentioned groups, or in multicomponent mixtures comprised of members in each of the aforementioned groups, will also be effective in killing microorganisms. The free nitrogen fraction should be ideally below that of oxygen in order to maintain a lower reaction temperature.

More specific and relatively simple multicomponent mixtures that are effective sterilants as well as effective organic barrier passivation agents are listed below:

| Specific Multicomponent Mixtures Comprised of Fractions A + B (percent of fraction is by volume) | |
|---|---|
| Fraction A | Fraction B |
| $O_2$ (92–97%) | $CF_4$ (3–8%) |
| [$O_2$ (40%)—He (60%)] | $CF_4$ (0.25–3%) |
| [$O_2$ (8%)—$CF_4$ (92%)] | He (80%) |
| [$O_2$ (17%)—$CF_4$ (83%)] | He (80%) |
| [$O_2$ (83%)—$CF_4$ (17%)] | He (80%) |
| [$O_2$ (92%)—$CF_4$ (8%)] | He (80%) |

Many of the aforementioned gas mixtures are, in themselves, novel chemical compositions.

The plasma discharge through such a composite mixture will, for example, create both oxygen-bearing and fluorine, or chlorine-bearing active species simultaneously. The latter will predominantly be responsible for passivating the organic barrier, since fluorination or chlorination, rather than oxidation of the organic barrier is favored thermodynamically. Therefore, the take-up of fluorine or chlorine-bearing active species by the organic barrier of the pouch will be preferential. This will leave a relatively larger fraction of oxygen-bearing active species available for sterilization, since the latter cannot easily be taken up by a fluorinated or chlorinated surface.

In addition, sterilization by oxygen-bearing active species may be aided, for example, by simultaneously discharging an oxygen-containing and fluorine or chlorine containing gas residing inside the enclosing pouch. This gas had previously permeated through the organic barrier prior to the commencement of the discharge. This will create active species that contain both oxygen and fluorine or chlorine within the pouch directly. As previously described, the competition for take-up by the organic barrier (pouch) will be won by the fluorinating or chlorinating species, leaving a larger net concentration of active species containing oxygen to do an effective sterilizing job.

However, residual fluorine or chlorine-bearing active species within the pouch and not taken-up by it will also perform effective surface sterilization, since they are strongly chemically oxidizing agents. But, the fraction of fluorine or chlorine-containing gas in the original composite gaseous mixture, is substantially smaller than the oxygen-containing component. Thus, a major portion of microorganisms kill will be attributed to the oxygen-bearing species in the plasma. In either case, however, the end result is a continuous attack on the proteinaceous structure of the microorganism resulting in its degradation and fragmentation into gaseous products. This chemical action by the reactive plasma is to initially modify (denature) the proteinaceous network of the microorganism, disrupting its metabolism at a minimum, but more commonly impeding its reproduction.

In a sterilization method in which a load is exposed within a sterilization zone to active species of a plasma generated in a reaction zone operably associated with the sterilization zone, improved sterilization efficacy is obtained by contacting the plasma with a textured metal surface prior to contacting the load with those active species. This improvement is manifested by lower load temperatures and better kill ratios. The plasma reaction zone may be operably associated with the sterilization zone in accordance with any of the system configurations proposed within the sterilization art for use with either RF or microwave plasma-based systems.

A preconditioning step is often advantageous. Ideally, the plasma is formed from a sterilant precursor, notably hydrogen peroxide or a peracetic acid composition. It has been found advantageous for the sterilization load to be exposed to the sterilant precursor for a period (typically between about 10 minutes to about 8 hours, but usually below about 2 hours) prior to energizing that precursor to produce a plasma.

Among other things, this invention provides a method for the sterilization of a load comprising the steps of placing the load within a gas-tight confining chamber formed at least in part from a metal wall; evacuating the chamber to a substantially low pressure, and introducing a biocidal fluid in vapor or gas state into the chamber. The load is exposed to the biocidal fluid during a preconditioning phase. A plasma is then induced in the biocidal fluid within the chamber by the application of electrical energy. The plasma is maintained for a controlled period of time. A portion of the inner surface of the chamber is provided with a textured surface capable of increasing the steady state concentration of active species contacting the load.

In a sterilization method in which a load is exposed within a sterilization zone to active species of a plasma generated in a reaction zone operably associated with the sterilization zone, this invention provides an improvement by which biocidal fluid in vapor or gas state is introduced into the sterilization zone. The load is exposed to the biocidal fluid during a preconditioning phase. A plasma is then induced in the biocidal fluid within the chamber by application of electrical energy, preferably RF energy. The plasma is contacted with a textured metal surface prior to the active species of that plasma contacting the load.

DESCRIPTION OF THE DRAWINGS

In the drawing

FIGS. 6, 7, 8, 9, 10, 11, 12, 13 and 14 are cross sectional and side views of alternative embodiments;

DESCRIPTION OF PREFERRED EMBODIMENTS

Figure 1:
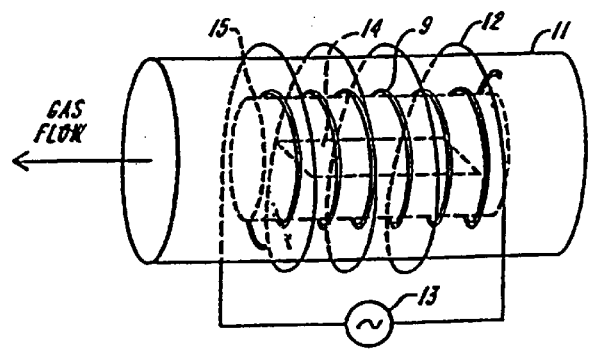
FIG. 1 is a general diagrammatic illustration of an apparatus suitable for use in the practice of this invention.

FIG. 1 is a general diagrammatic illustration of an RF excited discharge chamber of the type used in the process of this invention. The cylindrical chamber 11 is formed, in this instance, of glass or quartz and encloses within it the material 14 to be treated. The chamber is commonly connected to a mechanical vacuum pump (not shown) that establishes sub-atmospheric pressure conditions within the chamber. An exciter coil 12 couples RF energy from RF source 13 to the gas enclosed within the gas tight chamber creating a plasma therein.

Alternatively, a microwave discharge cavity operating at 2450 MHz may replace the RP exciter coil to couple power into the gas. With a suitable selection of a reducing gas, like hydrogen, or an oxidizing gas, such as oxygen, as a typical example, a discharge may be initiated and maintained within the chamber. In the gas plasma formed by such a discharge a number of excited species, both molecular and atomic, are formed. The interaction of these species with a surface of the device or material to be sterilized accomplishes the sterilization in the manner described above. The time duration of the process needed to achieve satisfactory sterilization will vary with other parameters of the discharge such as gas flow, pressure, RF or microwave power density, and load size.

Figure 2:
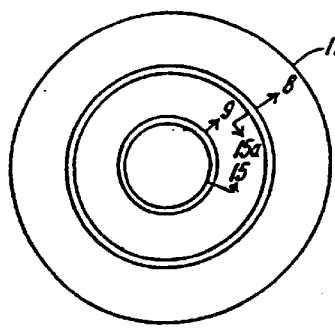
FIG. 2 is a cross sectional view of another apparatus suitable for use in the practice of this invention.

In the embodiment illustrated in FIG. 1 the apparatus includes an inner perforated metallic cylinder 15 mounted generally concentric with the long axis of the chamber 11, to form within the perforated cylinder a substantially glowless, field-free zone. The perforated cylinder 15 is electrically-floating and is cooled by recirculating a suitable coolant (e.g., a 50—50 mixture of water and ethylene glycol) through cooling coils 9 wrapped around the cylinder's length, to effect low sterilization temperatures (<70° C.). Still lower sterilization temperatures could be effected with two concentric perforated metallic cylinders 15 and 15a, surrounded by cooling coils 9 and 8, respectively, and enclosed by non-conducting chamber 11, as shown in FIG. 2. Energy coupling into this chamber is accomplished in a similar manner as described in FIG. 1. In a few cases, the configurations described in FIGS. 1 and 2 may not require cooling coils 8 and 9 if the plasma feed gas contains low levels of water vapor for the enhancement of sterilization efficiency and the reduction of processing cycle time and temperature.

The resultant glowless and field-free zone within the confines of the electrically-floating perforated cylinders could be ascribed to electrical faraday-cage effects, coupled with catalytic deactivation of active species, which are the precursors of visible emission, on the metallic surface of the perforated cylinder.

Figure 3:
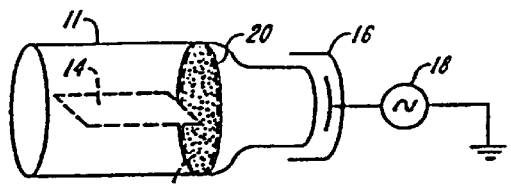
FIG. 3 is a generally diagrammatic illustration of another apparatus suitable for use in the practice of this invention.

When, as illustrated in FIG. 3, a microwave energy source 18 at for example, 2540 MHz. is employed in lieu of the RF generator 13, the perforated metallic cylinder cannot be mounted concentric about the long axis of the chamber. Instead, the microwave cavity 16 is mounted at one end of a metallic or non-metallic chamber 11, and a perforated metallic shield 17 cooled by coolant-recirculating coils 20 may be placed just beyond it toward the opposite end of the chamber, spanning the entire diameter cross section of the chamber, thus creating a field-free and glowless reactive zone immediately below it and away from the microwave cavity. These arrangements permit material 14 placed within this zone to be generally isolated from electrically charged species, while allowing the electrically neutral reactive plasma species, such as, for example, oxygen radicals, to interact with the surface of the material to be sterilized. In this manner, sterilization is commonly effected at substantially lower process temperatures.

Alternatively, the perforated metallic shield 17 may be removed, if microwave cavity 16 is remotely located from material 14.

Microwave discharges lend themselves to this mode of operation, since the effectiveness of neutral active species generated in such a discharge survive substantial distances downstream, and away from, the microwave cavity itself. This is a direct consequence of the higher population of electrons in microwave plasmas, and consequently the higher degree of ionization and dissociation in these discharges. Also, microwave plasma electric probe measurements indicated plasma potentials nearly equal to ground potential, thereby practically eliminating energic particle bombardment during processing. This mode of operation is thus well suited for low temperature exposure of heat-sensitive devices and material, even for extended periods of sterilization time.

In the most preferred embodiments, the chamber is formed of a metallic electrically grounded and water-cooled outer shell with either a single internal perforated cylindrical shield, as shown in FIG. 1, or perhaps with two such metallic shields, as shown in FIG. 2, which may be also purposely cooled, the RF energy being coupled, in this latter configuration, between the two conducting perforated cylinders. In either case, conditions for low plasma potentials will prevail, with the discharge glow being confined to the space between the inner wall of the chamber and the surface(s) of the perforated cylinder(s), leaving the work volume defined by the inner perforated cylinder substantially field-free, void of the plasma glow, and at a relatively low operating temperature.

Figure 4:
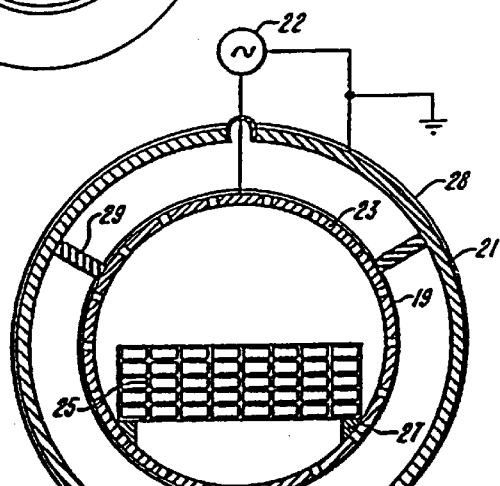
FIG. 4 is a cross sectional view of another embodiment of a sterilization chamber for use in the practice of the invention.
Figure 5:
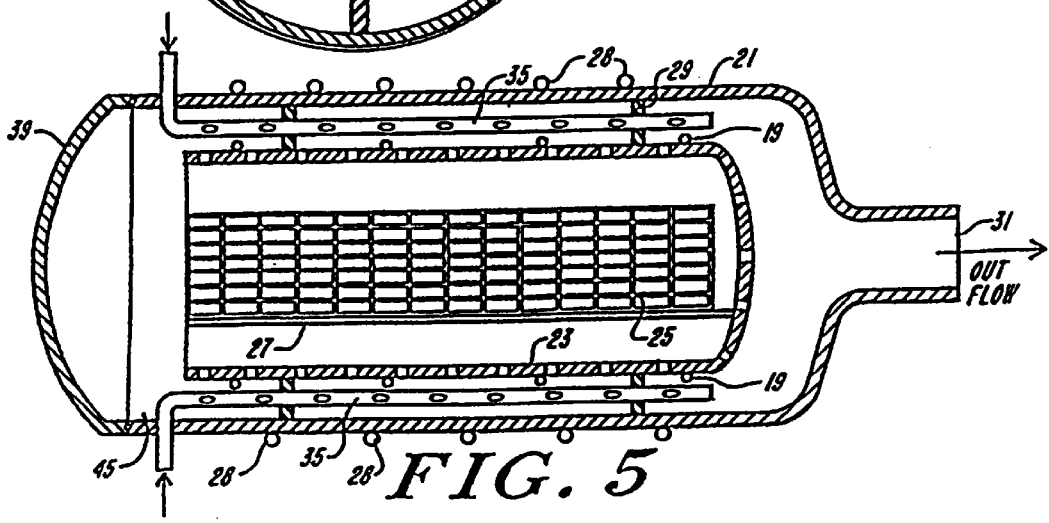
FIG. 5 is a side view of the apparatus of FIG. 4.

One such chamber configuration is illustrated in FIGS. 4 and 5. The cylindrical outer wall 21, typically formed of aluminum or stainless steel, is maintained at ground potential and serves as the chamber enclosure. This enclosure may be water-cooled with the aid of cooling coils 28 wrapped around it. Suitable dimensions for this chamber are a diameter of 36" and a length of 48". A metallic perforated inner cylinder 23 cooled by cooling coils 19 is mounted on insulating spacers 29 within the chamber so that it is positioned generally parallel with the long axis of the outer wall 21 of the chamber and concentric with it. These spacers may be formed of any suitable non-reactive and insulating type of material such as ceramic. The cylinder perforations are typically 2.5–4 mm diameter holes spaced in all directions from one another by approximately 0.5 cm in a triangulated manner. Longitudinal support rails 27 are fastened to the inner wall of the perforated cylinder 23 to support a wire basket 25 in which the materials and devices to be sterilized are placed. A suitable RF source 22 is coupled between the grounded outer chamber wall 21 and the perforated inner cylinder 23. Usually this RF source should be capable of producing an RF output in the range 0.01 to 0.1 W/cm$^3$ at frequencies in the 10–100 kilohertz or 13–27 megahertz range.

As illustrated in FIG. 5, an evacuation port 31 at the end of cylinder 21 is connected to a pump (not shown) and provides for suitable evacuation of the chamber and for continuous gas flow during the sterilization process. The gas supplied for the discharge is generally flowed through the chamber by means of perforated diffusion tubes 35. Alternately, gas may be introduced into the chamber via a gas dispersion device (not shown) mounted behind chamber door 39 from the inside.

Material to be sterilized may be placed within wire basket 25 resting on rail 27 through the entry port behind chamber door 39. Chamber door 39 may be any suitable closure that can be conveniently opened and closed and left in a sealed position during evacuation and the gas discharge operation.

FIG. 6 illustrates a second preferred embodiment of the apparatus for practicing the process of the invention. In this configuration, the outer chamber wall 21 may be water-cooled by cooling coils 28, is again formed of metal, such as electrically grounded aluminum or stainless steel, and is of similar dimensions to that illustrated in FIG. 4. Mounted within the chamber is an inner concentric cylinder 43 formed of a perforated metal which may be purposely cooled by cooling coils 30, and is supported on insulating support struts 46. The spacing between the inner wall of the chamber and the perforated interior cylinder may range typically from 10 to 17 cm, where the chamber has an I.D. of 36". A second metallic perforated cylinder 41 is concentrically mounted intermediate between the inner perforated cylinder 43 and the inner wall of the chamber and may also be cooled by cooling coils 19. This second perforated cylinder is supported on insulating struts 47 and is spaced typically 4 to 7 cm away from the inner perforated cylinder 43. The insulator struts may again be formed of a ceramic material. Mounted on the interior of the inner concentric cylinder 43 are support rails 27 for carrying a wire basket which would contain the materials to be sterilized. Both the outer chamber wall 21 and the inner perforated cylinder 43 are electrically connected to point of potential reference (ground). Electrical connections would most usually be made through ceramic seal feedthroughs 48 and 49. The intermediate cylinder 41 is electrically connected to one side of the RF power supply 22, the other side of which is connected to the point of potential reference.

While a variety of conventional RF sources may be used, the most typical value for the RF frequency is 13.56 MHz or, alternatively, 10–100 KHz. As in the embodiment of FIG. 5 longitudinally extending gas diffusion tubes 35 may be employed to provide the gas to the interior of the chamber. Typically each tube would have holes of diameter between 0.5 and 1.5 mm, spaced approximately 1" apart along its length. The hole diameters closer to the gas source would be of the smaller diameter. Alternatively, gas inlets may be provided behind chamber door 39. As indicated in the embodiments of FIGS. 4, 5 and 6 the perforated inner cylinders may be open-ended at both ends or, may be closed with the same perforated stock as is used to form the cylinder(s). The sterilization chambers shown in FIGS. 4, 5 and 6 may be connected to a microwave discharge source, typically operating at 2540 MHz, in lieu of an RF energy source. In this case, the concentric perforated metallic cylinder(s) may be replaced by a single perforated shield in accordance with the operational description given for FIG. 3.

FIG. 7 illustrates a third preferred embodiment of the apparatus for practicing the process of the invention. In this diagrammatic description the outer chamber wall 21 is again formed of metal, such as aluminum or stainless steel, and is of similar dimensions to that illustrated in FIG. 4. Mounted within the chamber are two planar, metallic, electrodes 50 and 51, preferably constructed of aluminum which may be coated with insulating aluminum oxide. The gap 52 between electrodes 50 and 51, is adjustable by virtue of the movable bottom electrode 50. Terminals A and B are connected to the electrodes via an insulating feedthrough 48. The outer end of these terminals may be connected to an RF source (not shown) in such a way that when terminal B is connected to a ground potential, terminal A must be connected to the RF source, or vice versa, providing for an electrical symmetrical configuration. The work load to be sterilized is placed on lower electrode 50.

It is important to maintain the distance between the electrodes always smaller than the distance of the RF-powered electrode's edge to the grounded chamber's wall. This enables a well defined and intense plasma glow to be confined to space 52 between the electrodes and prevents deleterious sparking. The electrode material may also be made of the perforated stock previously mentioned. However, it is desirable to have the RF-powered electrode made of solid stock to enable very efficient water-cooling of that electrode. The bottom electrode may also be made of solid stock to enable a cooler surface upon which the work load to be sterilized will be placed. This chamber will commonly be evacuated to 10–100 microns Hg before gas introduction via the perforated gas diffusion tubes 35. Practical device sterilization can be obtained with process parameters for gas flow rates in the range 20 to 3000 scc/m, corresponding to a total sterilization reaction pressure of 10–5000 microns Hg, at a range of RF power densities of 0.0125 to 0.08 W/cm$^3$. Process exposure times will depend on load size and are commonly in the range 2 to 120 min.

FIG. 8 illustrates in diagrammatic form yet another preferred embodiment for practicing the process of the invention. The outer wall of chamber 21 is again formed of metal, such as aluminum or stainless steel maintained at ground potential, and is of similar dimensions to that illustrated in FIG. 4. Mounted within the chamber is a single planar, metallic, electrode 50, preferably constructed of aluminum which may be coated with insulating aluminum oxide to reduce RF sputtering. This electrode is commonly connected to an RF source in the MHz range and carries the work load to be sterilized. This electrode has commonly a total surface area which is at least four times smaller than the total internal surface area of the grounded chamber, to effect a low plasma potential mode of operation. This arrangement, coupled with low power densities (see below) is conducive to very low sterilization temperatures.

This electrical configuration is usually referred to as asymmetric and is conducive to generating an extremely uniform plasma glow filling the entire volume of the processing chamber. It is also responsible for the development of a characteristic accelerating potential at the surface of electrode 50, associated with a thin "dark space" through which positive plasma ions will accelerate and impinge on the electrode and the work load it normally carries.

This arrangement is recommended for hard-to-sterilize materials almost exclusively, particularly for sterilization of metallic devices replete with a high density of cracks and crevices.

The main advantage of this process chamber configuration is its ability to render efficient sterilization at relatively low power densities in the range of 0.0125–0.025 W/cm$^3$.

This configuration is also easily scalable as a function of work load size.

This process chamber commonly operates with at least an order of magnitude lower pressure than the pressure for chambers described in FIGS. 1 through 7, while the gas dispersion tubes 35 are similar in construction to those previously mentioned. To prevent RF sputtering of electrode 50 due to positive ion bombardment, it may either be hard-anodized or alternatively aluminum oxide spray-coated.

One particular sub-configuration to that described in FIG. 8 is illustrated in FIG. 9. In this configuration chamber 21 is water-cooled by cooling coils 28 and contains a perforated metallic enclosure 71 totally surrounding and containing electrode 70. This enclosure may be cooled by coolant-recirculating coils 72 and may be connected to a separate RF source 22a, of a different frequency than that of source 22. This perforated enclosure may be equipped with an open/close hinging mechanism (not shown) to enable access for material to be sterilized to be placed on electrode 70 contained within enclosure 71. This yields the beneficial effect of being able to separately control the abundance of sterilizing active species and their impinging energy. RF power applied to electrode 70, which may or may not include a negative DC potential from a separate DC supply, (not shown), will control energy of ion impingement, while RF power applied to the auxiliary perforated enclosure 71, will control active species abundance.

With this configuration, RF power sources operating at 100 KHz and 13.56 MHz may be used in the various possible permutations. Interesting results are obtained by mixing both frequencies while being applied to a single element. Commonly, one frequency has to be applied at a higher power fraction, usually around 90% of the total applied power to the same element. Such interesting process results were obtained when the two different frequencies were mixed and applied to electrode 70 in the absence of any auxiliary perforated enclosure. The mixed frequency concept also lends itself to low power density sterilization in the range 0.0125 to 0.025 W/cm$^3$, with the advantage of maintaining the overall temperature relatively low (below 50° C.), particularly when electrode 70 is water-cooled by cooling coils 74.

It is worth noting that the auxiliary perforated enclosure 71 ought to be of high mesh transparency to allow the plasma glow to extend past it and contact electrode 70. Best operating conditions will be obtained for the smallest surface area of this perforated metallic enclosure. In a few instances, this metallic enclosure was connected to ground, yielding effective sterilization data.

FIG. 10 illustrates diagrammatically a preferred embodiment for practicing the process of the invention under atmospheric pressure conditions in ambient air. In this configuration no vacuum capability is required. Material to be sterilized is placed on grounded and water-cooled conveyor belt 62 which sweeps the load across the discharge gap created between conveyor belt 62 and RF-powered and water-cooled electrode 61. Electrode 61 cooled by cooling coil 76 produces a large plurality of needle-like discharges which create individual discharge sparks toward the counter grounded electrode 62. The larger the gap between the electrodes, the higher the power needed to initiate the discharge in air.

Sterilization is effected due to ozone formation following the discharge of oxygen in the ambient air. Power density requirements in the range 5 to 15 W/cm$^2$ are not uncommon.

Maintaining a controlled relative humidity of 50 to 60% in the discharge gap will facilitate initiation of the discharge and promote atomic oxygen generation. The latter serves as a precursor to ozone formation, the final desired sterilant in this configuration.

Ozone toxicity inhibits wide acceptance of such a corona discharge in air for the purpose of medical or dental device sterilization. Alternatively, therefore, the RF-powered electrode 61 may assume a configuration comprised of multiple open nozzles 65, capable of dispersing oxidizing gases immediately adjacent to conveyor belt 62. In this configuration the discharge would still be created in ambient air, however the dispersion through the open-nozzles 65 of a judiciously selected feed gas will increase the local concentration of its active species 63 relative to that of ozone. In this manner, sterilization would be attributable to active species derived from any feed gas introduced into the hollow RF-powered electrode 61 and not to the deleterious ozone gas.

The dispersing nozzles 65 may assume different configurations. For example, separate nozzle tubes may be inserted into a hollow section of electrode block 61, which may or may not be of different material than electrode block 61. These tubes may also be screwed into the electrode block 61 for easy replacement. A typical hole size for each individual nozzle is in the range 0.015–0.040".

The advantages of this discharge configuration are mainly in terms of system simplicity and in the context of continuous operation, coupled with the ability to easily change the residence time of a work load within the discharge gap.

Disadvantages are commonly associated with erosion and degradation of both electrode block 61 and conveyor belt 62. Electrode 61 should be constructed from oxidation-resistant materials (e.g., tungsten, molybdenum or alloys thereof). The grounded conveyor belt electrode 62 may be constructed from stainless steel or any other suitable nickel-coated metal, and may be cooled by cooling coil 77. Alternatively, a dielectric conveyor belt may be used. With such an arrangement, the insulating belt is mounted in close proximity to a stationery grounded and fluid cooled metallic block serving as the counter electrode. The conveyor belt ought to be resistant to electrical punch-through and be constructed from fluorinated, fluorinated/chlorinated or fluorinated/chlorinated nitrogen-containing hydrocarbons (e.g., DuPont products). High melting polyimides or Kalrez-like synthetics may serve as alternate construction materials for the conveyor belt. Kalrez is a polyimide manufactured by DuPont.

Other configurations are illustrated in FIGS. 11, 12, 13 and 14. These configurations are preferred embodiments for practicing the process of the invention with narrow bore and elongated tubulation, almost exclusively. They are particularly designated for the treatment and sterilization of fiber optics-based tubulations as, for example, endoscopes, proctoscopes, angioscopes or bronchoscopies, having internal diameters as small as 2 mm and an overall length of about 1000 mm.

The outer wall of elongated chamber 91 is made preferentially of non-metallic material (e.g., glass, ceramic) but, may also be comprised of a metallic/non-metallic structure. The chamber has a minimum internal diameter of one and one half times that of the outside diameter of elongated tubulation 94. The inner and outer surfaces of narrow bore tubulation 94 need to be treated or sterilized. Both ends of narrow and elongated chamber 91 are hermetically plugged with gas permeable but microorganism-impervious membranes 99 (e.g., Tyvek). This arrangement ensures the dynamic flow of an active plasma through and over tubulation 94, and also secures its aseptic condition after sterilization and during prolonged storage.

To effect sterilization or treatment of the inner and outer surfaces of tubulation 94, it is inserted into chamber 91 either bare or sealed within a gas permeable elongated pouch. The chamber is then plugged at both ends with membranes 99.

The chamber is subsequently inserted into exciter coil 92 (FIG. 11) whose terminals are connected to a suitable RF energy source like the one described with respect to FIG. 1.

In another arrangement, the chamber may be inserted within the air gap of capacitive plates 93 (FIG. 12) whose terminals are connected to a suitable RF energy source like the one described with respect to FIG. 1.

Alternatively, chamber 91 may be brought into close proximity to microwave cavity 16 (FIG. 13) whose terminal is connected to a suitable microwave energy source as described with reference to FIG. 3.

Figure 11:
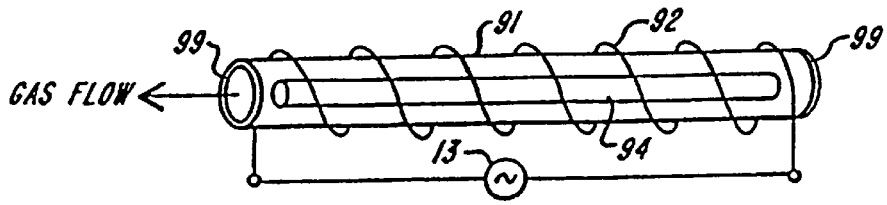
Figure 12:
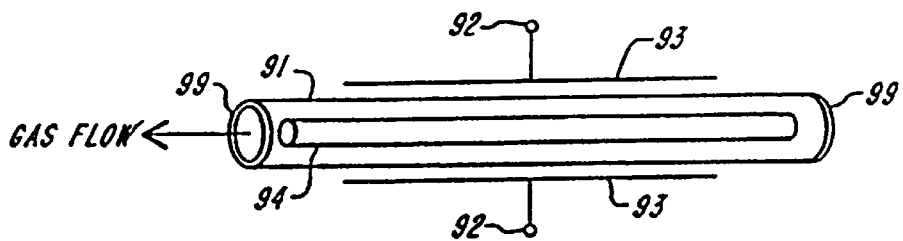
Figure 13:

In cases where the chamber is a metallic—non-metallic structure, the various energy sources described in FIGS. 11, 12 and 13 are coupled to the chamber via the non-metallic portion of the chamber.

In each of the configurations of FIGS. 11, 12 and 13, one end of elongated chamber 91 is temporarily vacuum-flanged to a gas delivery and monitoring system (not shown), while the other free end of the chamber is temporarily vacuum-flanged to a gas exhaust pumping system (not shown).

At the end of the sterilization or treatment cycle, the gas flow and the energy source are turned off, chamber 91 is disengaged from the power source and from both vacuum flanges and stored for future use of narrow bore tubulation 94.

For practical reasons, a plurality of chambers 91 may be employed in a parallel electrical arrangement simultaneously, either in an RF or microwave discharge hook-up.

Figure 14:
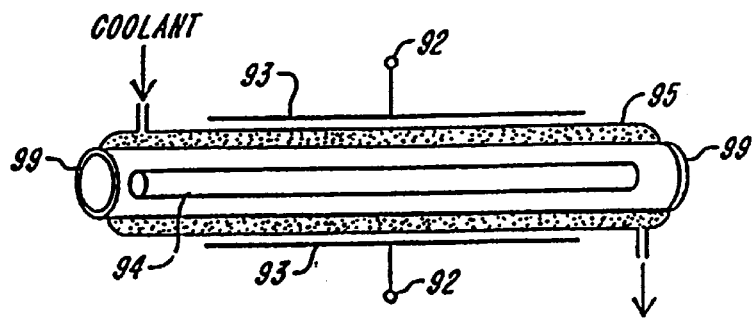

Chamber 91 may have a cooling jacket 95 around it as, for example, shown in FIG. 14. It is not mandatory that exciter coil 92 (FIG. 11) or capacitive plates 93 (FIG. 12) enclose or extend over the entire length of tubulation 94; the latter may be partially contained or not contained at all within coil 92 or capacitor plates 93.

Set forth below are specific examples of suitable operating parameters for effective sterilization employing various apparatus as illustrated in the figures. The particular chamber and corresponding configuration, are referenced in the examples.

However, for each of the examples the general technique involved was one in which the material to be sterilized was placed directly in the reaction chamber, or placed within a Tyvek/polyethylene pouch which itself was sealed and placed in a wire basket within the reaction chamber.

The materials used for verification of sterilization effectiveness were "Attest" vials obtained from 3M Company, or "Spordex" bacterial test strips obtained from the American Sterilizer Company, each vial or "Spordex" envelope contained a bacterial strip having an original spore population of not less than $1 \times 10^6$ Bacillus Subtilis var Niger per strip, but more commonly in the range $2.2$–$4.0 \times 10^6$ spores/strip. The strips contained the permeable plastic vials were not brought into contact with the culture solution contained in any of the vials prior to sterilization. The vials were placed within the Tyvek/polyethylene bags during the plasma sterilization, alongside devices or instruments to be sterilized. The bags were always sealed during the sterilization process.

For each example the chamber was first evacuated to an initial low pressure level after the materials (in the bags or pouches) were placed within it. The chamber was thereafter filled with the appropriate gas prior to striking the discharge, and the gas continued to flow through the chamber at a controlled rate to establish a steady state sterilization pressure. The discharge was initiated by the application of RF or microwave power as indicated. The discharge was maintained for a controlled time period at the end of which the power was turned off, the chamber was first evacuated, then backfilled with air through a bacteria retentive filter, and later opened and the samples removed. The temperature within the chamber during the process was maintained at less than 70° C., and more typically around 25° C. to 65° C., as sensed by an iron-constantan, type "J", thermocouple circuitry and monitored by an analog temperature meter.

Subsequent to the tests, the spore strips in the "Attest" vials where brought into contact with the self-contained culture solution and incubated for 72 hr, at the end of which period microorganism growth or no growth would be indicated by the resultant color of the culture solution. Alternatively, the spore strips were submitted to an independent testing laboratory which performed a total plate count on the sample strips using a procedure in which 100 milliliters of sterile deionized water were added to each strip in a sterile whirl-pak bag. The bag was then placed in a lab blender for 10 minutes. One 10 milliliter aliquot of sample, a duplicate one milliliter sample, and two consecutive $10^{-1}$ dilutions were plated using Tryptic Soy Agar. The plates were then incubated at 30–35° C. for 72 hours. After incubation, the plates were read and recorded, and the results calculated on a Colony Forming Unit (CFU) basis.

EXAMPLE 1

With metal chamber and internal uncooled perforated cylinder, (FIG. 4)
Gas: $O_2$(Pure)
Flowrate: 20 scc/min
Pressure: 0.30 torr
Power Density: 0.050 W/cm$^3$
Exposure time: 60 min.
Temperature : 66° C.
Resultant microbial count: <10 CFU (below sensitivity limit of counting technique)
Percent kill: 99.9999%
Metal chamber dimensions: 8"D×8"L

EXAMPLE 2

With metal chamber and internal cooled perforated cylinder, (FIG. 4)
Gas: $O_2$(Pure)
Flowrate: 20 sec/min
Pressure: 0.30 torr
Power Density: 0.050 W/cm$^3$
Exposure time: 60 min.
Temperature : 32° C.
Percent kill: Total kill
Metal chamber dimensions: 8"D×8"L

EXAMPLE 3

With Pyrex chamber and internal cooled perforated cylinder, (FIG. 1)
Gas: $O_2/CF_4$ (8%)
Flowrate: 36 scc/min Pressure: 0.35 torr
Power Density: 0.050 W/cm$^3$
Exposure time: 60 min.
Temperature: 34° C.
Resultant microbial count: <10 CFU (below the sensitivity limit of counting technique)
Percent kill: 99.9999%
Pyrex chamber dimensions: 8"D×8"L

EXAMPLE 4

With metal chamber and two uncooled internal perforated cylinders, (FIG. 6)
Gas: O$_2$
Flowrate: 20 scc/min
Pressure: 0.30 torr
Power Density: 0.050 W/cm$^3$
Exposure time: 60 min.
Temperature: 76° C.
Percent kill: Total kill
Metal chamber dimensions: 8"D×8"L

EXAMPLE 5

With metal chamber and two cooled internal perforated cylinders, (FIG. 6)
Gas: O$_2$
Flowrate: 20 scc/min
Pressure: 0.30 torr
Power Density: 0.050 W/cm$^3$
Exposure time: 60 min.
Temperature: 36° C.
Resultant microbial count: <10 CFU
Percent kill: 99.9999%
Metal chamber dimensions: 8"D×8"L

EXAMPLE 6

With Pyrex chamber and cooled internal perforated cylinder, (FIG. 1)
Gas: He(59.85%)—O$_2$(39.90%)—CF$_4$(0.25%)
Flowrate: 48 scc/min
Pressure: 0.35 torr
Power Density: 0.050 W/cm$^3$
Exposure time: 60 min.
Temperature: 31° C.
Resultant microbial count: <10 CFU
Percent kill: 99.9999%
Pyrex chamber dimensions: 8"D×8"L

EXAMPLE 7

With metal chamber and two cooled internal perforated cylinders, (FIG. 6)
Gas: O$_2$(60%)—He(40%)
Flowrate: (total) 42 scc/min
Pressure: 0.35 torr
Power Density: 0.050 W/cm$^3$
Exposure time: 60 min.
Temperature: 32° C.
Resultant microbial count: <10 CFU
Percent kill: 99.9999%
Metal chamber dimensions: 8"D×8"L

EXAMPLE 8

With Pyrex chamber and cooled internal perforated cylinder, (FIG. 1)
Gas: O$_2$(pure)
Flowrate: 25 scc/min
Pressure: 0.30 torr
Power Density: 0.015 W/cm$^3$
Exposure time: 30 min.
Temperature: 26° C.
Percent kill: Total kill
Pyrex chamber dimensions: 8"D×8"L

EXAMPLE 9

With Pyrex chamber and uncooled internal perforated cylinder, (FIG. 1)
Gas: O$_2$(pure)
Flowrate: 25 scc/min
Pressure: 0.30 torr
Power Density: 0.015 W/cm$^3$
Exposure time: 30 min.
Temperature: 83° C.
Percent kill: Total kill
Pyrex chamber dimensions: 8"D×8"L For the following examples, the initial spore population was 4×10$^6$ spores/strip.

EXAMPLE 10

With microwave discharge and internal perforated metallic shield disc, (FIG. 3)
Gas: Helium/Argon (50%/50%, v/v)
Flowrate (total): 80 scc/min
Pressure: 0.40 torr
Power Density: 0.015 W/cm$^3$
Exposure Time: 90 min Temperature: 29° C.
Resultant Microbial Count: 1.7×10$^2$ CFUs
Percent Kill 99.9993
Pyrex chamber dimensions: 6"D×10"L

EXAMPLE 11

With microwave discharge and internal perforated metallic shield disc, (FIG. 3)
Gas: Oxygen (Pure)
Power Density: 0.015 W/cm$^3$

| Flow Rate (scc/min) | Pressure (torr) | Resultant Exposure (min) | Microbial Count (CFUs) | Percent Kill (%) |
|---|---|---|---|---|
| 30 | 0.20 | 20 | 5.8 × 10$^5$ | 77.6923 |
| 30* | 0.22 | 45 | <10 | 99.9999 |

Temperature: 24–30° C.
*Sample enclosed in barrier cloth, 2-ply, American Textiles, Inc.
Pyrex chamber dimensions: 6" D × 10" L

EXAMPLE 12

With Pyrex chamber and two uncooled internal perforated cylinders, (FIG. 1)
Gas: O$_2$
Flowrate 70 scc/min
Pressure: 0.275 torr
Power Density: 0.016 W/cc
Exposure Time: 45 min
Temperature: 92° C.
Percent Kill: Total Kill
Pyrex chamber dimensions: 9"D×13"L
Sample was the standard sterilization test pack provided by guidelines of the Association for the Advancement of Medical Instrumentation (AAMI)

EXAMPLE 13

With Pyrex chamber and two cooled internal perforated cylinders, (FIG. 1) Same experimental conditions as in Example 12

Temperature: 54° C.
Percent Kill: Total Kill
Sterilization test pack employed was according to AAMI guidelines.

EXAMPLE 14

With Pyrex chamber and uncooled internal perforated cylinder.
Gas: $O_2$
Flowrate 70 scc/min
Pressure: 0.275 torr
Power Density: 0.014 W/cc
Exposure Time: 30 min
Temperature: 85° C.
Percent Kill: Total Kill
Pyrex chamber dimensions: 9"D×13"L

EXAMPLE 15

With Pyrex chamber and cooled internal perforated cylinder, (FIG. 1) Same experimental conditions as in Example 14
Temperature: 47° C.
Percent Kill: Total Kill
Pyrex chamber dimensions: 9"D×13"L

EXAMPLE 16

With Pyrex chamber and cooled internal perforated cylinder, (FIG. 1) Same experimental conditions as in Example 14
Exposure time: 2¼ hr.
Temperature: 51° C.
Percent Kill: Total Kill
Pyrex chamber dimensions: 9"D33 13"L

EXAMPLE 17

With Pyrex chamber and uncooled internal perforated cylinder.
Gas: $O_2$ (containing 500 ppm of $H_2O$)
Flowrate: 70 scc/min
Pressure: 0.275 torr
Power Density: 0.015 W/cc
Exposure Time: 20 min.
Temperature: 61° C.
Percent Kill: Total Kill
Pyrex Chamber Dimensions: 9"D×13"L

EXAMPLE 18

With Pyrex chamber (9"D×13"L) and cooled internal perforated metallic cylinder, (FIG. 1)
Gas: Dry and moist Oxygen, Nitrogen and Argon ($H_2O$ level: 300 ppm)
Flowrate: 100 scc/min
Pressure: 0.280–0.300 torr
RF Power Density: 0.020 W/cc
Temperature: 38–57° C.
Sample Size per Experiment: Ten (10) 3M "Attest" vials with 4×10⁶ spores/strip in each vial, placed in a sealed Tyvek/polyethylene pouch.

| Exposure Time (min) | Dry $O_2$ | Moist $O_2$ |
|---|---|---|
| 30 | 4 vials - total kill | 9 vials - total kill |
| 45 | 6 vials - total kill | 10 vials - total kill |
| 60 | 8 vials - total kill | — |
| 75 | 10 vials - total kill | — |
| | Dry $N_2$ | Moist $N_2$ |
| 30 | 0 vials - total kill | 0 vials - total kill |
| 45 | 0 vials - total kill | 0 vials - total kill |
| 60 | 1 vial - total kill | 2 vials - total kill |
| 75 | 2 vials - total kill | 3 vials - total kill |
| | Dry Ar | Moist Ar |
| 30 | 0 vials - total kill | 0 vials - total kill |
| 45 | 0 vials - total kill | 1 vial - total kill |
| 60 | 1 vial - total kill | 2 vials - total kill |
| 75 | 2 vials - total kill | 3 vials - total kill |

EXAMPLE 19

With Pyrex chamber (9"D×13"L) and cooled internal metallic perforated cylinder, (FIG. 1)
Gas: $O_2$
Flowrate: 100 scc/min
Pressure: 0.280 torr
RF Power Density: 0.020 W/cc
Exposure time: 70–105 min
Temperature: 50° C.
Samples:
  a. 24-inch long PVC tubing with internal diameter of 11 mm and wall thickness of 2 mm.
  b. 24-inch long silicone rubber tubing with internal diameter of 3/16" and wall thickness of 1/16". Spore strip was placed in middle of tubing at approximately 18-inch from either free end of tubing. The latter was bent into a U-shape and placed within a Tyvek/polyethylene pouch and sealed prior to plasma sterilization.
Percent Kill: Total Kill

EXAMPLE 20

With Pyrex chamber (9"D×13"L) and cooled internal perforated metallic cylinder, (FIG. 1)
Gas: Dry and Moist Nitrogen-Oxygen and Argon-Oxygen Mixtures ($O_2$:5–15%);
($H_2O$ level: 300 ppm)
Flowrate: 100 scc/min
Pressure: 0.275–0.300 torr
RF Power Density: 0.020 W/cc
Temperature: 34–53° C.
Sample Size per Experiment: Ten (10) 3M "Attest" vials with 4×10⁶ spores/strip in each vial, placed in a sealed Tyvek/polyethylene pouch

| Exposure Time (min) | Dry $N_2$—$O_2$ | Moist $N_2$—$O_2$ |
|---|---|---|
| 30 | 1 vial - total kill | 1 vial - total kill |
| 45 | 1 vial - total kill | 1 vial - total kill |
| 60 | 2 vials - total kill | 3 vials - total kill |
| 75 | 3 vials - total kill | 4 vials - total kill |

-continued

| Exposure Time (min) | Dry Ar—O$_2$ | Moist Ar—O$_2$ |
|---|---|---|
| 30 | 1 vial - total kill | 1 vial - total kill |
| 45 | 1 vial - total kill | 2 vials - total kill |
| 60 | 3 vials - total kill | 4 vials - total kill |
| 75 | 4 vials - total kill | 5 vials - total kill |

Certain embodiments of this invention rely upon neutral actives species produced by subjecting a vapor of a peracid material to an electrical discharge at reduced pressure. The apparatus and methods described in this disclosure may be operated generally in harmony with the previous examples, using either RF or microwave energy to create a plasma from either hydrogen peroxide or peracetic acid vapors.

A preconditioning step may be practiced prior to plasma generation. The articles to be sterilized are thereby first exposed to vapors of peracetic acid or an equivalent peracetic precursor material. Thereafter, peracetic vapors may be used as a precursor for generation of a plasma. An electrical shield, such as a perforated metal cage or plate, is positioned between the plasma and the articles to exclude charged species from direct contact with the articles.

Peracetic acid (PAA) solutions may be prepared either with high residual acetic acid, or with high residual hydrogen peroxide. In either case, peracetic acid is vaporized at a non-decomposing temperature, typically about 60° C. Flow lines should be kept at slightly higher temperature, typically below about 65° C. By comparison, hydrogen peroxide may be vaporized at 74° C. with the flow lines maintained at 77° C. The flow line should ideally be kept about 3° C. higher than the selected peracetic acid vaporization temperature.

Figure 15:
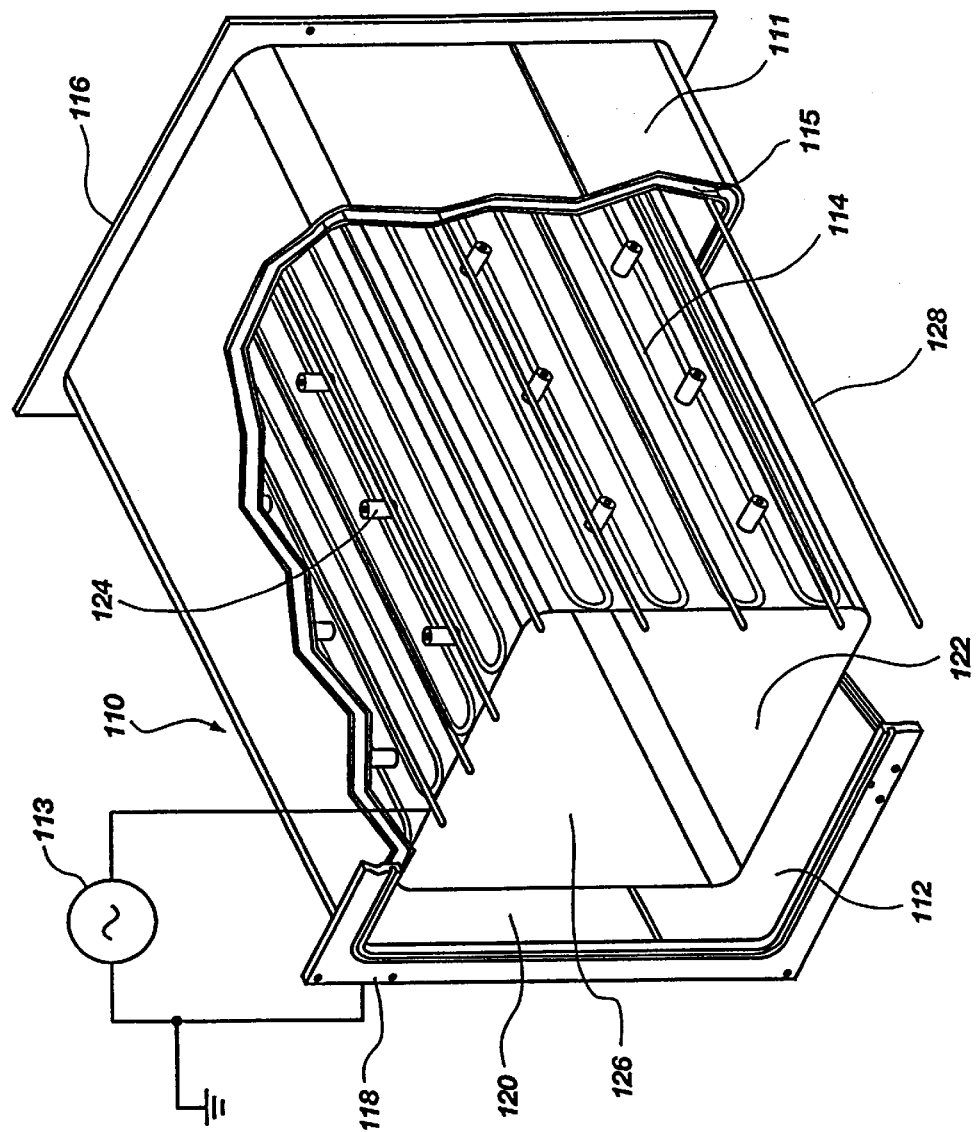
FIG. 15 is a fragmentary pictorial view, partially broken away of a sterilization apparatus of this invention.

FIG. 15 illustrates an RF sterilizer, generally 110 of this invention constructed within a cylindrical outer shell 111 having an approximately rectangular cross section. An inner shell 112 is concentric with the outer shell, and is connected to the grounded side of an RF generator 113. It thus serves as a grounded electrode for the system. The inner surface of the shell 112 is roughened, as by sand blasting. The chamber and its contents may be preheated by flowing a heat-exchange medium through the coils 114 or the internal volume 115 between the liners 111, 112. Space is provided between a rear flange 116 and a front flange 118 to accommodate insulation (not shown). Plasma is generated in the annular space 120 between the grounded shell 111 and an inner electrode 122 connected to the ungrounded side of the power supply 113. Ceramic spacers 124 are positioned as shown within the space 120 between the inner shell 112 and the inner electrode 122. The inner electrode 122 is perforated with openings selected to pass neutral gaseous species or vapor but to exclude charged plasma species. It may thus be viewed as a Faraday cage.

Figure 16:
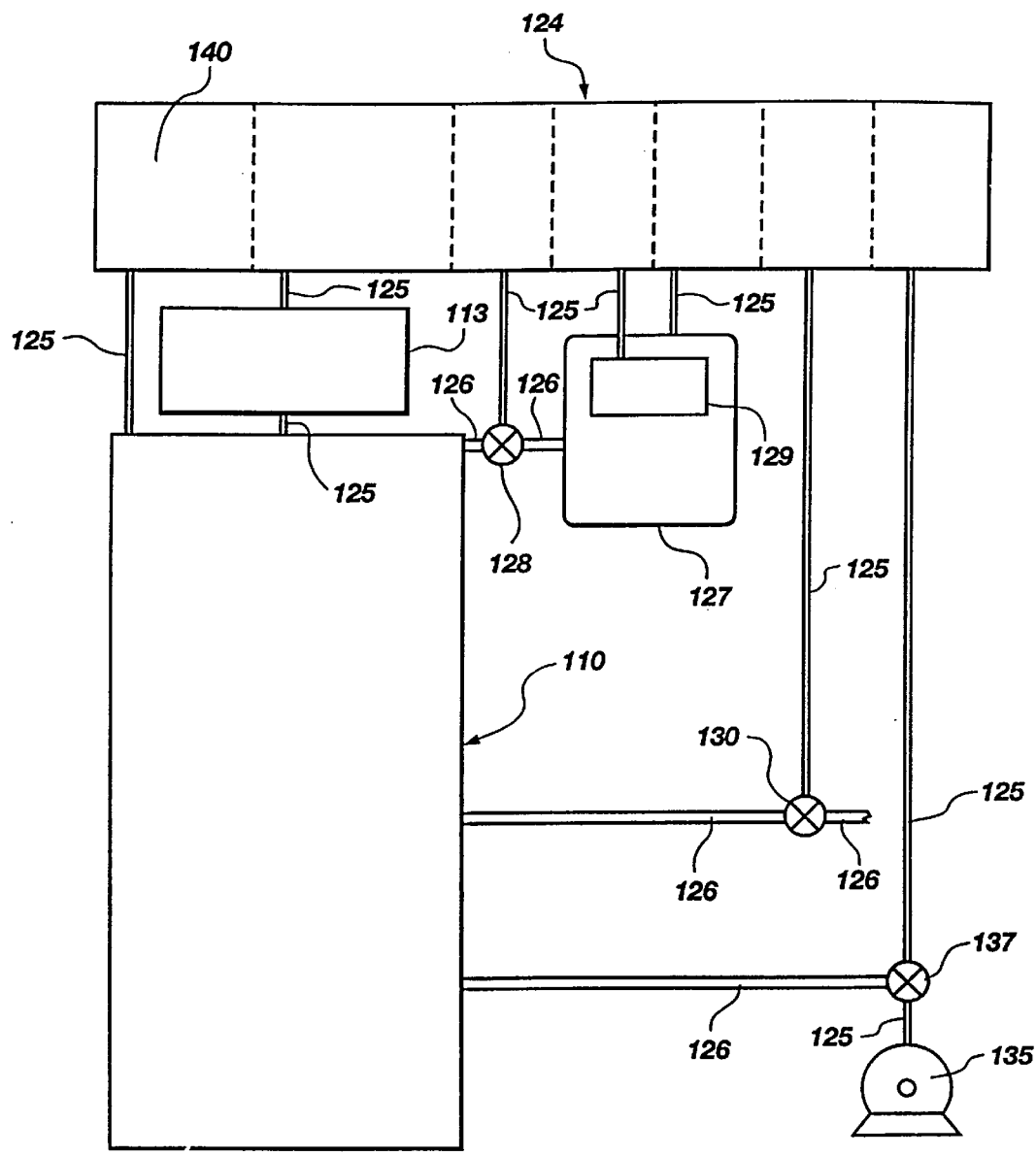
FIG. 16 is a schematic diagram of a typical sterilization system of this invention.

The sterilizer 110 is shown within a system by FIG. 16. A programmable logic controller (PLC), generally 124, or other suitable circuitry, is connected through cables 125 to the power supply 113 and other components of the system as shown. Fluid flow between system components is accommodated by appropriate conduits 126. Precursor vapors are supplied from a source 127 to the annular space 120, and thus the interior 126 of the perforated inner electrode 122. These vapors are distributed through diffusion tubes 128 positioned around the perimeter of the inner electrode 122. Vapor flow is through a control valve 128 opened and closed by the controller 124. Liquid sterilant precursor is vaporized by a heater 129 associated with the source 127 and cycled appropriately by the controller 124. A pump 130, also responsive to the controller 124, circulates coolant through coils 114 mounted to the inner electrode 122. Pressure within the chamber 120, 126 is adjusted by operation of a vacuum pump 135 and associated control valve 137, both of which are turned on and off by the controller 124. Pressure and temperature sensors (not shown) are positioned strategically within the sterilizer 110 to provide input signals to the controller 124.

A dwell preconditioning phase may decrease the volume of sterilant precursor required per cycle. A preconditioning step is also considered beneficial to the sterilizing efficacy of the system. Referring to FIGS. 15 and 16, a preconditioning phase may consist of the following steps:

1. The chamber shells 111,112 and electrode 122 are heated to a preselected temperature (around 40° C.).
2. The vacuum pump 135 is operated to establish a base pressure (typically 500 microns).
3. A pressure controller 140 associated with the PLC 124 is adjusted to a first (lower) setpoint (typically 2 torr), and vapor (typically hydrogen peroxide or peracetic acid) is introduced through the diffusion tubes 128 to allow this setpoint to be achieved.
4. After the pressure within the chamber 120, 126 has equilibrated at the first selected setpoint level, the pressure controller 140 is assigned a second (higher) setpoint (typically 6.5 torr), and the controller 124 operates to adjust the control valve 137 to achieve this second setpoint.
5. After the pressure equilibrates at the second setpoint, and subsequent to any selected timed dwell period, the pressure controller 140 is assigned a third setpoint (typically approximately the same as the first, or lower, setpoint, e.g., 2 torr), and the valve 137 to the vacuum pump 135 is again adjusted by the controller 124 to achieve this third setpoint.
6. Steps 4 and 5 may be repeated for a predetermined time period.
7. After the predetermined time period has expired, the pressure controller 140 establishes an operating setpoint (typically 600 microns) for plasma processing.
8. When the operating setpoint is reached, the plasma is ignited within the space 120 by operation of the power supply, and permitted to run for the predetermined cycle time.

EXAMPLE 21

The efficacies of hydrogen peroxide and peracetic acid solutions in the sterilization process of this invention were studied as part of a series of statistical designed experiments.

AAMI EO Test Packs: Modified AAMI Standard EO packs were prepared in which the BI strip was removed from its glassine wrap before processing. Three strips were placed in each syringe, and the syringe was closed at its large end with the standard rubber stopper. A second syringe was prepared containing one MDT Biosign CLBI (results reported as fractional negative). The syringes were placed adjacent to one another and were wrapped in a huckabuck towel per the AAMI EO Test Pack standard. The entire assembly was placed in a Baxter 'Tower Dual-Peel' 7.5"× 13" paper-plastic peel pouch, which was subsequently heat sealed.

Statistical Design of Experiments: This example is based upon both Taguchi and Greco-Latin Square experimental designs in accordance with standard statistical design of experiment techniques [CSS:Statistica, StatSoft, Tulsa, Okla.]. These experimental designs permitted variation of four parameters over four discrete levels (Greco-Latin Square) or five parameters over four discrete levels (Taguchi L'16 design). The resultant data, reported as log reduction, is analyzed to provide mean values for each of the parameters at each parameter level. Also provided are ANOVA and correlation results (for reduction vs. exposure time), which evaluate the statistical validity of the data.

Experimental: For all of the experiments, the packs were placed in a rectangular sterilization chamber (FIG. 15) in an overlapping configuration (paper to paper and plastic to plastic. The packs were allowed to overlap only to the extent required by the size of pouches and the basket in which they were placed. This arrangement provided a maximum overlap of about ⅔ of the pack width. The packs were placed approximately in the middle of the chamber and filled the area of the basket from front to back.

In cases where no RF was applied, after the cycle was complete, the strips were placed in a sterile residual neutralizing solution for ten minutes, followed by immersion in sterile water for another ten minutes. For hydrogen peroxide, the neutralizing solution was catalase in phosphate buffer and for peracetic acid, ~5 uM sodium thiosulfate was used.

The process variables explored in these studies have been: RF on/off, base pressure (minimum pressure experienced by the load in initial pumpdown), process pressure (pressure at which the plasma is actually run), exposure time (plasma phase only-precondition was held fixed at 30 minutes with default pulsing parameters), sterilant precursor (hydrogen peroxide and peracetic acid), and biological indicator organism and lot. The plasma excitation frequency was 40 kHz throughout at a power level of 5 kW.

Results:

The results are reported separately as mean values for each parameter in a given experimental design. Based on these results, it is possible to choose an optimal value for each process parameter.

Base Pressure

The base pressure is the initial pressure to which the system is pumped down before a commencement of the preconditioning phase. Using Greco-Latin Square and Tuguchi L'16 designed experiments data were taken on efficacy at base pressures of 100, 200, 250, 300, 400, 500 microns and 1 and 1.5 torr. Analysis of the experimental data generated confirmed 500 microns as the optimal base pressure for a wrapped goods cycle.

Precursor: Both peracetic acid (5% and 15%) and hydrogen peroxide (50% and 70%) were tested. The lower concentrations of each precursor has been determined to be less efficacious than the higher concentrations. The mean results for 15% peracetic acid and 70% hydrogen peroxide were 2.8 log reduction and 3.1 log reduction, respectively. However, in this series, the peracetic acid was run at the same vaporization temperature (74° C.) as was the hydrogen peroxide. Peracetic acid decomposes fairly rapidly at this temperature. Accordingly, a direct comparison was made with the peracetic acid vaporization temperature set at 60° C. (See Example 22.)

Plasma pressure: The Taguchi L'16 designed experiment included variation of plasma pressure as one of its parameters. The values used were 500, 600, 700, and 800 microns. Analysis of this experimental set shows 600 microns plasma pressure to be the most efficacious for the process. ANOVA analysis of this data shows it to be statistically valid with $F=18.55$ and a p-value of 0 to 6 decimal places.

RF: This series of experiments confirmed the improved rate of kill due to the presence of a plasma vs. that observed when only the sterilant precursor was used in the process. The Taguchi L'16 experimental data set yields a mean log reduction with RF off of 0.2 log, while with RF on, the mean reduction was 4.35 log. This result is also confirmed by the Greco-Latin Square experimental set, in which the mean log reduction for Bstm with RF off was 1.13, while the mean log reduction with RF on was 4.26. For Bg, the results were 3.10 for RF off and 5.33 with RF on.

Exposure Time: In the Taguchi L'16 experimental set, testing was done at exposure times of 40, 50, 60, and 70 minutes. Within a reasonable approximation, the log reduction values fall on an essentially straight line (correlation coefficient 0.9559). This trend was also observed for Bg kill in the Greco-Latin Square experimental set (correlation coefficient of 0.965). For Bstm in that set, near log-linear kinetics were observed (correlation coefficient of 0.9643). The D-values that result from these analyses, although not done at optimal conditions, range between 10.53 and 10.87 minutes for Bstm and 7.87

EXAMPLE 22

A direct comparison of 15% peracetic acid and 70% hydrogen peroxide sterilant precursors was made by exposing AAMI standard EO test packs for 45 minutes to plasma induced by 40 kHz excitation frequency with 5 kW RF power. The procedure consisted of processing four AAMI standard EO test packs using either sterilant precursor at a plasma pressure of 600 microns, using a 30 minute preconditioning phase with lower and upper setpoints of 2 torr and 6.5 torr, respectively, a base pressure of 100 microns and an exposure time of 45 minutes. No glassine was used on the BI strips (Bstm, $10^6$ spore population, MDT lot 601). The peracetic acid was vaporized at 60° C. vs. a 74° C. hydrogen peroxide vaporization temperature. In this measurement set, 70% hydrogen peroxide and 15% peracetic acid were seen to be essentially identical in efficacy (5.43 mean log reduction vs. 5.57, respectively).

In sterilizers in which a plasma is generated within a volume in which a sterilization load is also present, the load is exposed to infrared, visible and (ultraviolet) light, as well as the active plasma species desired for sterilization. Plasma sterilization processes are run at very low pressures. Radiant heat from both the plasma and any surfaces heated by the plasma may heat the load above a temperature suitable for the load. It has been discovered that positioning a textured surface adjacent the situs at which plasma is generated (for example, a portion of the interior surfaces defining a plasmas reaction zone) is generally effective in lowering both load heating and the steady state temperature achievable within the sterilizer.

The positive influence of a roughened reactor surface on the steady-state concentration of active species available for dry sterilization procedures has also been observed. This effect has been observed in processes employing various gaseous and vaporous sterilization precursors. Increased roughness, within the range tested, generally increases the steady state concentration of active species in a plasma generation zone, and the steady-state concentration of neutral active species penetrating the perforated shield to reach the glowless, substantially field free sterilization zone favored by this disclosure.

Processes conducted in accordance with any of the examples of this disclosure would be expected to benefit from structural modifications which provide roughened surfaces in contact with the plasma, preferably while it is being generated.

EXAMPLE 23

A number of sterilization cycles were run under the conditions specified in Example 21 in a system such as that illustrated by FIG. 16. A sterilizer of the type illustrated by FIG. 15 was used. The inner shell was constructed of 316 SST with a 220–300 grit polish followed by sand blasting with #46 aluminum oxide at 80–100 psig. to produce a roughened surface.

These tests demonstrated improved sterilization efficacies with the inner surface of the shell 112 roughened in this fashion as compared to similar control cycles in which this surface had a polished finish. They also demonstrated lower load temperature after equivalent exposure durations under similar conditions with the inner surface of the shell 112 roughened in this fashion as compared to similar control cycles in which this surface had a polished finish.

Specifically, with process conditions of 0.600 torr pressure, 15% peracetic acid feed vapor, RF power density of 0.031 W/cm$^3$, 40 kHz RF frequency and exposure times of 90 minutes, load temperatures fell from 70° C. with a polished chamber to 57° C. in the roughened chamber. The roughened chambers thus appear to absorb radiant energy from a plasma glow. It is thus available to select plasma chemistries that produce active biocidal species under conditions in which they do not transfer to the load as readily as they undergo nonradiative decay.

Several other cycles were run in reaction chambers structured as illustrated by FIGS. 4 and 5, but with roughened cylindrical metal chamber inserts composed either of SST 304 (stainless steel alloy) or 6061T6 (aluminum alloy). The inserts were positioned effectively to replace the outer chamber designated 21 in the figures. These cycles demonstrated that both surface roughness and chamber material have an impact on process efficacy. The following table reports results obtained using an oxygen plasma with feed gas entering the chamber at a flow rate of 250 sccm, a reaction pressure of 0.650 torr, RF power density of 0.097 W/cm$^3$ and the load being AAMI standard EO test packs. The Spore strips used were *B. subtilis* v. niger, with an initial population of 4×10$^6$. Exposure time was 105 minutes, and the final processing temperature was 60° C.

TABLE

| Chamber Material | Roughness (Grit Size) | Results (Fractional Survivors) |
| --- | --- | --- |
| SST 304 | 120 | 4/9 |
| SST 304 | 180 | 1/9 |
| SST 304 | 250 | 6/9 |
| SST 304 | 300 | 7/9 |
| SST 304 | 600 | 9/9 |
| Al 6061T6 | 180 | 8/9 |
| Al 6061T6 | 600 | 9/9 |

The SST-lined chambers had significantly greater efficacy in these cycles than did the aluminum-lined chambers. The effect of grit size is also apparent, with the best results achieved with a 180 grit size. Both coarser and finer grit sizes produced less efficacious results.

A preferred apparatus of this invention includes a gas-confining chamber constructed and arranged for containing an electrical discharge. The portion of the chamber in contact with the plasma has a textured surface. For purposes of this disclosure, the term "textured" is by comparison to a polished or unaltered mill finish, such as is conventionally produced by cold rolling. An article-containing (sterilization) zone is positioned to receive substantially neutral active species from the electrical discharge, and a barrier structure transparent to substantially neutral active species and opaque to charged species is positioned between the sterilization zone and the discharge. The barrier structure, typically a perforated inner electrode as shown by FIG. 15, comprises a first electrode, and the chamber comprises a second electrode, the first and second electrodes constituting means for initiating the electrical discharge.

A portion of the second electrode is provided with a textured surface which is rough compared to an unaltered mill surface finish of the material from which that portion is constructed. The gas-confirming chamber may be or include a plasma-reaction zone defined in part by an inner surface of the chamber. That inner surface, which sometimes includes the entire inner surface of the gas-confining chamber, is preferably constructed of a metal selected from the group consisting essentially of stainless steel and aluminum alloys. Other metals are operable, but are often impractical or uneconomical to use. The textured portion is roughened by means equivalent to sand blasting with aluminum oxide grit, the precise texturing method employing being a matter of choice. Various chemical and physical etching techniques are within contemplation. A stainless steel metal surface textured equivalent to a surface sand blasted with aluminum oxide grit having a grit size of between about 120 and about 300 is presently preferred. Sandblasting at about 100 psig for a period of between about one half hour to about 2 hours is generally sufficient to produce an effective texturing for purposes of this invention.

EXAMPLE 24

A reactor such as that illustrated by FIGS. 4 and 5 was provided with grounded metal electrode inserts. Inserts were constructed of various stainless steel and aluminum alloys. Cycles were run to compare the performance of the reactor when provided with inserts of different surface textures. Selected inserts were subjected to conventional sand blasting with aluminum oxide grit sizes of 120, 180, 250, 300, 450 and 600. The inserts with textured surfaces uniformly produced improved sterilization efficacy compared to similar inserts having polished surfaces.

What is claimed is:

1. In a sterilization method wherein a load is exposed within a sterilization zone to active species of a plasma generated in a reaction zone operably associated with said sterilization zone; the improvement which comprises:
   contacting said plasma with a textured metal surface while contacting said load with said active species, said textured metal surface forming at least a portion of an inner surface of a gas confining chamber which contains said plasma.

2. An improvement according to claim 1 wherein said plasma is generated within a gas-confining chamber containing said reaction zone, said plasma being induced by the application of RF energy.

3. An improvement according to claim 2 wherein said chamber is defined by a surface of aluminum or stainless steel and said sterilization zone is defined by a perforated metallic shield constructed to be transparent to electrically neutral plasma species and opaque to electrically charged plasma species.

4. An improvement according to claim 1 wherein said plasma is generated within a reaction zone separated from said sterilization zone by a barrier constructed to be transparent to electrically neutral plasma species and opaque to electrically charged plasma species.

5. An improvement according to claim 4, wherein said reaction zone comprises an annular volume surrounding said sterilization zone.

6. An improvement according to claim 5, wherein said plasma is induced by the application of RF energy.

7. An improvement according to claim 4, wherein said plasma is induced by the application of microwave energy.

8. An improvement according to claim 7, wherein said barrier is in the form of a perforated metal plate interposed between said reaction zone and said sterilization zone.

9. An improvement according claim 4, wherein said load is exposed to a biocidal fluid within said sterilization zone during a preconditioning period, and thereafter energy is applied to said precursor to produce said plasma.

10. An improvement according to claim 9, wherein said biocidal fluid is selected from the group consisting essentially of hydrogen-peroxide solutions and peracetic acid solutions.

11. An improvement according to claim 10, wherein said sterilization load is exposed to said biocidal fluid for a period of between about 10 minutes and about 8 hours prior to energizing that biocidal fluid to form a plasma.

12. An improvement according to claim 1 conducted within apparatus comprising:

a gas-confining chamber constructed and arranged for containing an electrical discharge which includes substantially electrically neutral active species;

an article-containing zone positioned to receive substantially neutral active species from said electrical discharge; and a barrier means between said article-containing zone and said discharge, said barrier means being transparent to substantially neutral active species and opaque to charged species;

said barrier means comprising a first electrode and said chamber comprising a second electrode, said first and second electrodes constituting means for initiating an electrical discharge within said chamber;

a portion of said second electrode having a textured surface which is rough compared to an unaltered mill surface finish of the material from which said portion is constructed.

13. An improvement according to claim 12, wherein said gas-confining chamber includes a plasma reaction zone defined in part by an inner surface of said chamber, said inner surface being constructed of a metal selected from the group consisting essentially of stainless steel and aluminum alloys.

14. An improvement according to claim 12, wherein said portion is roughened by means equivalent to sand blasting with aluminum oxide grit.

15. An improvement according to claim 14, wherein said portion is a stainless steel metal surface textured equivalent to being sand blasted with aluminum oxide grit having a grit size of between about 120 and about 300.

16. An improvement according to claim 1, comprising the steps of:

placing medical devices and/or materials within a gas-tight confining chamber wherein said chamber is formed at least in part from a metal wall and includes an internal perforated metallic element positioned within said chamber;

evacuating said chamber to a substantially low pressure, and introducing a biocidal fluid into said chamber;

initiating an electrical discharge in said biocidal fluid within said chamber by application of RF energy between said metal chamber wall and said internal perforated metallic element, creating a gas plasma; and maintaining said gas plasma for a controlled period or time, said perforated metallic element creating a field free and glowless volume within said chamber, said devices and materials being placed within said field free and glowless volume;

a portion of the inner surface of said chamber being provided with a textured surface.

17. An improvement according to claim 16, wherein said plasma is initiated adjacent an inner surface of said chamber, and said inner surface has a texture which is rough compared to an unaltered mill surface finish of the material from which said surface is constructed.

18. An improvement according to claim 17, wherein said inner surface is constructed of a metal selected from the group consisting essentially of stainless steel and aluminum alloys.

19. An improvement according to claim 17, wherein said inner surface is roughened by means equivalent to sand blasting with abrasive grit.

20. An improvement according to claim 19, wherein said inner surface is a stainless steel metal surface textured equivalent to being sand blasted with aluminum oxide grit having a grit size of between about 120 and about 300.

* * * * *